United States Patent [19]

Maloney

[11] Patent Number: 4,791,913
[45] Date of Patent: Dec. 20, 1988

[54] OPTICAL VALVULOTOME

[75] Inventor: Patrick M. Maloney, El Toro, Calif.

[73] Assignee: Baxter Travenol Laboratories, Inc., Deerfield, Ill.

[21] Appl. No.: 132,150

[22] Filed: Dec. 14, 1987

[51] Int. Cl.⁴ ............................................. A61B 1/06
[52] U.S. Cl. ...................................................... 128/6
[58] Field of Search ........................... 128/3, 4, 5, 6, 7

[56] References Cited

U.S. PATENT DOCUMENTS

| | | | |
|---|---|---|---|
| 1,680,490 | 8/1928 | Wappler | 128/7 |
| 1,901,731 | 3/1933 | Buerger | 128/7 |
| 2,621,651 | 12/1952 | Wallace | 128/4 |
| 3,871,365 | 3/1975 | Chikama | 128/5 |
| 3,896,793 | 7/1975 | Mitsui et al. | 128/6 |
| 4,027,510 | 6/1977 | Hiltebrandt | 128/6 X |
| 4,132,227 | 1/1979 | Ibe | 128/4 |
| 4,178,920 | 12/1979 | Cawood, Jr. et al. | 128/4 |
| 4,222,380 | 9/1980 | Terayama | 128/4 X |
| 4,254,762 | 3/1981 | Yoon | 128/4 |
| 4,257,420 | 3/1981 | Terayama | 128/4 X |
| 4,372,295 | 2/1983 | Heckele | 128/4 |
| 4,374,523 | 2/1983 | Yoon | 128/6 X |
| 4,421,106 | 12/1983 | Uehara | 128/4 |
| 4,471,766 | 9/1984 | Terayama | 128/6 |
| 4,474,174 | 10/1984 | Petruzzi | 128/4 |
| 4,499,899 | 2/1985 | Lyons, III | 128/6 X |
| 4,537,209 | 8/1985 | Sasa | 128/4 |
| 4,593,680 | 6/1986 | Kubokawa | 128/4 |
| 4,607,620 | 8/1986 | Storz | 128/4 |
| 4,641,634 | 2/1987 | Storz | 128/4 |
| 4,656,999 | 4/1987 | Storz | 128/4 |
| 4,683,874 | 8/1987 | Acquista | 128/6 |

FOREIGN PATENT DOCUMENTS

| | | | |
|---|---|---|---|
| 0159033 | 10/1985 | European Pat. Off. | |
| 759088 | 8/1980 | U.S.S.R. | 128/4 |

Primary Examiner—William H. Grieb
Attorney, Agent, or Firm—Gordon L. Peterson

[57] ABSTRACT

An instrument comprising an elongated control handle having a passage extending therethrough, an elongated flexible catheter body having at least one lumen and a distal end coupled to the control handle and an elongated flexible member extending through the passage and into the lumen and having a distal end portion. A tool is coupled to the distal end portion of the flexible member, and the tool is capable of performing a medical task within a patient. An elongated flexible image-transmitting member extends through the passage of the control handle and into the lumen. A position controller is mounted for sliding movement along the control handle and is drivingly coupled to the flexible members so that the axial positions of the tool and the image-transmitting member can be adjusted with respect to the distal end of the catheter body.

12 Claims, 3 Drawing Sheets

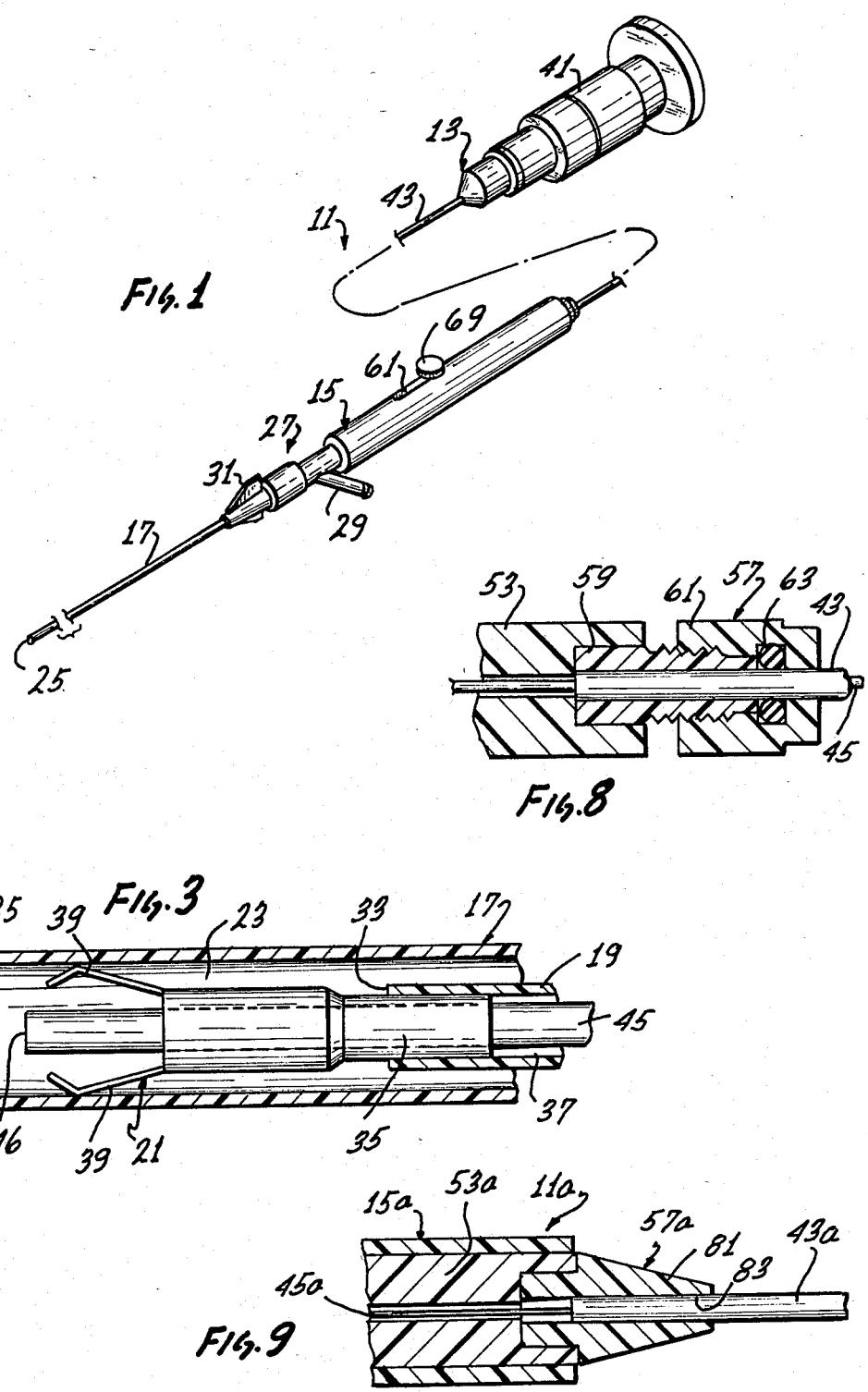

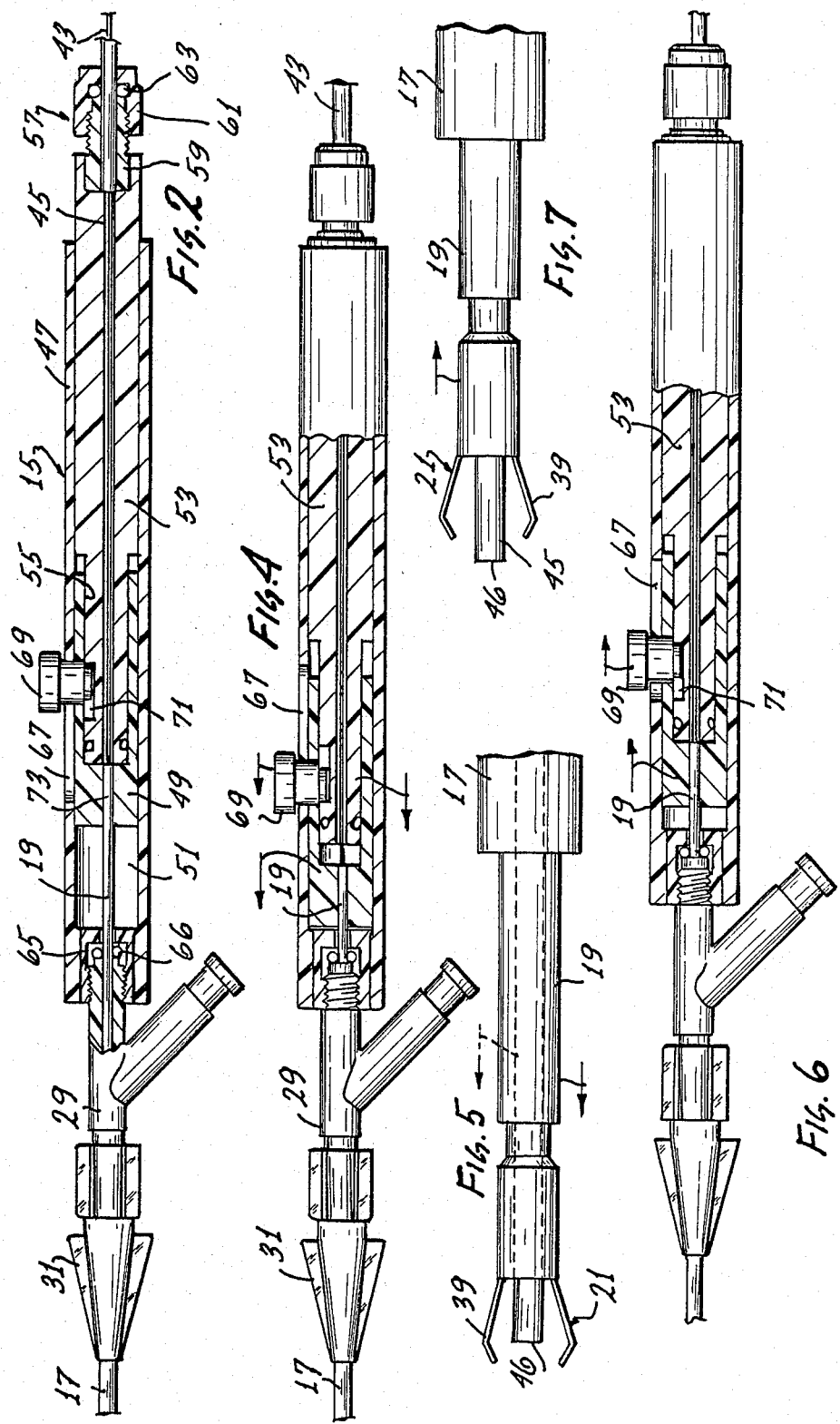

OPTICAL VALVULOTOME

BACKGROUND OF THE INVENTION

Certain large veins within the legs contain valves in the nature of check valves which prevent blood in these veins from settling into the lower regions of the legs and the feet. It is sometimes necessary or desirable to remove these valves, and this may occur in a medical procedure in which these veins are converted to arteries.

The valves can be removed using a valvulotome which comprises a catheter body which can be advanced through the vein of interest to a position adjacent the valve to be removed. The valvulotome includes a tool, which may comprise axially extending prongs, which can be advanced through the valve to disrupt and at least partially remove it. For this purpose, it is known to advance the catheter body with the tool fully retracted into the lumen of the catheter body to a position adjacent the valve and then extend the tool from the distal end of the catheter body so that it can perform its valve disrupting function.

To enable the physician to observe the procedure, the valvulotome may also include an endoscope. The endoscope includes an image-transmitting fiber extending through the catheter body and movable out the distal end of the catheter body under the control of the physician. Accordingly, the valvulotome may provide for independent axial adjustment in the positions of the tool and the distal end of the image-transmitting fiber.

One problem in use of the valvulotome is in positioning of the tool and the image-transmitting fiber. For example, during insertion of the catheter into the vein and the advance of the catheter through the vein, the tool and image-transmitting fiber would be entirely within the catheter body. During the medical procedure, the tool, and perhaps the distal end portion of the image-transmitting fiber, would be advanced out of the catheter body. Finally, during withdrawal of the catheter, the image-transmitting fiber and the tool would be within the catheter body. Accordingly, it is necessary for the physician to change the position of these components a multiplicity of times during the procedure. Unfortunately, prior art instruments of this type do not facilitate the positioning of these members to the extent desired.

SUMMARY OF THE INVENTION

This invention provides an instrument with a control handle which can be easily operated with one hand thereby leaving the other hand of the physician free for other purposes. With the control handle of this invention, the relative axial positions of both the tool and the image-transmitting fiber can be easily adjusted with one hand. Another feature of this invention is that the relative axial movements of the tool and image-transmitting fiber can be programmed to follow a specified sequence which is ordinarily desired for a particular medical procedure thereby further simplifying operation of the instrument for the physician. Although the features of this invention are particularly adapted to be embodied in a valvulotome, they are equally applicable when the tool performs some task other than disruption of the valves of veins.

An instrument constructed in accordance with the teachings of this invention has a control handle. So that the control handle can be easily grasped, it is preferably elongated. The control handle may also have a passage extending through it. An elongated, flexible catheter body having at least one lumen and a distal end is coupled to the control handle, and an elongated flexible member extends into the lumen. A tool which is capable of performing a medical task within a patient is coupled to the distal end portion of the flexible member. An elongated, flexible image-transmitting member extends through the passage and into the lumen.

A position controller is mounted for movement on the control handle. To facilitate ease of operation and one-handed operation, the position controller is preferably mounted for sliding movement along the control handle. The position controller is drivingly coupled to both of the flexible members so that the axial positions of the tool and the image-transmitting member can be easily adjusted with respect to the end of the distal end of the catheter body.

Although the coupling means for the flexible members can take different forms, it can advantageously include a slide mounted for sliding movement in the passage of the control handle, with the slide coupled to at least one of the flexible members. In one preferred construction, this coupling means includes first and second slides coupled to the flexible members, respectively, and mounted for sliding movement in the passage of the control handle. Both of the slides are coupled to the position controller with one of the slides being coupled to the position controller with lost motion. This construction is further enhanced by mounting one of the slides for sliding movement within the other of the slides. The control handle may have a generally axially extending slot, and the position controller preferably projects through the slot.

The position controller is movable from a first position to a second position and then to an intermediate position between the first and second positions. One feature of this invention is that the flexible members can be coupled to the position controller such that the tool and the image-transmitting member will move to programmed positions as the position controller is moved to its positions. In a preferred construction, this coupling connection is such that the tool and the image-transmitting member are within the lumen in the first position, the tool and distal end of the image-transmitting member are out of the lumen with the distal end of the image-transmitting member being more proximal than the tool in the second position, and the tool and the distal end of the image-transmitting member are out of the lumen with the distal end of the image-transmitting member being positioned distally of the tool in the intermediate position.

The endoscope preferably includes a flexible tube, and the image-transmitting member extends through the flexible tube. The flexible tube is attached to one of the slides and extends proximally of the control handle. The tube does not allow axial movement of the image-transmitting member within the tube. To allow the endoscope to be reused, the tube can be releasably attached to the slide. Alternatively, if the entire instrument is to be disposable, the attachment between the tube and the slide may be permanent.

The position controller may comprise one or more position control elements. With a single position control element, the relative axial movements of the tool and image-transmitting member can be precisely programmed as a function of the position of the single position control element. On the other hand, by using two position control elements, some variation in the program can be obtained.

The invention, together with additional features and advantages thereof, may best be understood by reference to the following description taken in connection with the accompanying illustrative drawing.

BRIEF DESCRIPTION OF THE DRAWING

FIG. 1 is an isometric view of an instrument constructed in accordance with the teachings of this invention.

FIG. 2 is an elevational view partially in section of the control handle and adjacent regions of the instrument, with the position controller in the retracted position.

FIG. 3 is an enlarged fragmentary sectional view of the distal end portion of the catheter body showing the relative axial positions of the tool and image-transmitting fiber with the position controller in the retracted position.

FIG. 4 is a view similar to FIG. 2 with the position controller in the extended position.

FIG. 5 is a side elevational view of the distal tip region of the catheter body showing the relative positions of the tool and image-transmitting fiber when the position controller is in the extended position.

FIG. 6 is a view similar to FIG. 2 with the position controller in the intermediate position.

FIG. 7 is a view similar to FIG. 5 showing the relative positions of the image-transmitting fiber and the tool when the position controller is in the intermediate position.

FIG. 8 is an enlarged fragmentary sectional view showing the region of the instrument adjacent the proximal end of the scope slide.

FIG. 9 is an enlarged fragmentary sectional view showing an alternate construction for the region of the instrument adjacent the proximal end of the scope slide.

DESCRIPTION OF THE PREFERRED EMBODIMENTS

Figure 10:
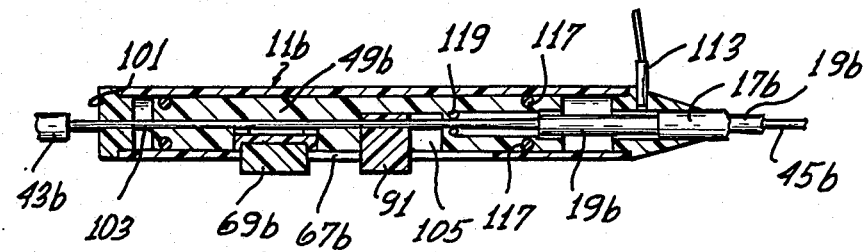
FIG. 10 is a sectional view through an alternate form of control handle which includes two position control elements.

FIG. 1 shows an instrument 11 which generally comprises an endoscope 13, a control handle 15, a catheter body 17, a tubular flexible member 19 (FIG. 3) and a tool 21 suitably attached to the distal end of the flexible member 19. In the illustrated embodiment, the instrument 11 is a valvulotome in that the tool 21 is adapted to disrupt the valves carried by large veins in the legs. Of course, the tool 21 could be replaced with tools for other purposes, if desired.

The catheter body 17 is elongated and flexible and is sized to be received within the relatively large veins of the leg. Although various constructions are possible, in this embodiment, the catheter body 17 has a single lumen 23 (FIG. 3) which extends axially completely through the catheter body. The catheter body 17 has a distal end 25, and a coupling 27 couples the proximal end of the catheter body 17 to the distal end of the control handle 15. The coupling 27 can take different forms, and in this embodiment, it comprises a Y-fitting 29 and a hub 31 attached by threads in a conventional manner to the distal end of the Y-fitting 29.

The tubular flexible member 19 extends from a location within the control handle 15 into the lumen 23. The tubular flexible member 19 has a distal end portion 33, and the tool 21 is coupled to the distal end portion 33. Although this can be accomplished in different ways, in this embodiment, the tool 21 includes a tubular collar 35 wedged into a passage 37 which extends through the tubular flexible member 19. The tool 21 also includes a plurality of generally axially extending fingers or prongs 39 (FIG. 3) of metal or other suitable material. As shown in FIG. 3, the tool 21 is sized to be received within the lumen 23.

The endoscope 13 includes an eyepiece housing 41 (FIG. 1) containing conventional endoscope optical elements, a flexible tube 43 coupled to the eyepiece housing and an elongated flexible member 45 extending through the tube. The flexible member 45 includes an image-transmitting fiber or member and one or more illumination fibers. The flexible member 45 extends from the eyepiece housing 41 through the control handle 15 into the lumen 23.

The flexible member 45 extends into the passage 37 of the flexible member 19 as shown in FIG. 3. With this construction, the flexible members 19 and 45 are coaxial. The flexible member 45 terminates at a distal end 46.

The control handle 15 (FIGS. 1 and 2) includes an elongated, rigid, cylindrical sleeve 47 of plastic or other suitable material, a tool slide 49 slidable in a passage 51 which extends axially through the sleeve and a scope slide 53 slidable in both the passage 51 and in a passage 55 of the tool slide 49. The tube 43 is attached to the scope slide 53 in any suitable manner, such as with a Touhy-Borst adapter 57 (FIGS. 2 and 8). As shown in FIG. 8, the adapter 57 comprises a hollow bushing 59 received in, and adhesively attached to, a cavity in the proximal end of the scope slide 53, a collar 61 threadedly attached to the bushing, and a resilient O-ring 63 which can be axially compressed and radially expanded by the bushing and collar into contact with the tube 43 to firmly couple the tube 43 to the scope slide. By loosening the collar 61 to allow the O-ring 63 to relax, the tube 43, and hence the endoscope 13, can be detached from the control handle 15.

With this arrangement, the tube 43 moves with the scope slide 53. Also, because of the relatively long lengths of the tube 43 and the flexible member 45 and the relatively small clearance between these members, the flexible member 45 also moves with the scope slide 53.

A collar 65 is received within the distal end of the passage 51 and is adhesively attached to the sleeve 47. The flexible member 19 extends through an opening in the collar 65 into the Y-fitting 29. An annular seal 66 forms a liquid-tight seal around the flexible member 19. The sleeve 47 has an axially extending slot 67, and the control handle includes a position controller in the form of a position control element 69 which is attached to the tool slide 49 and which projects through the slot 67 and into a slot 71 on the periphery of the scope slide 53.

The position control element 69 can be moved from a retracted position (FIGS. 2 and 3) to an extended position (FIGS. 4 and 5) and then back to an intermediate position (FIGS. 6 and 7) which is intermediate the retracted and extended positions. In the retracted position, the position control element 19 is at the proximal end of the slot 67 and also at the proximal end of the slot 71. In this position, the prongs 39 and the distal end 46 of the flexible member 45 are both within the lumen 23 (FIG. 3). Preferably, although not necessarily, the distal end 46 is more distal than the prongs 39 to thereby prevent the tool 21 from interfering with the view obtained through the endoscope 13. In the retracted position, the instrument 11 is adapted to have the catheter body 17 advanced into the vein of interest to a site where a valve is to be removed and also for withdrawal of the catheter body from the vein.

By grasping the sleeve 47 with one hand, the physician can easily slide the position control element 69 forwardly with his thumb to the distal end of the slot 67. During the initial portion of this movement, the position control element 69 drives only the tool slide 49. The tool slide 49 receives a proximal end 73 of the tubular flexible member 19 and is attached thereto as by an adhesive, and so therefore, this distal movement of the tool slide moves the tool slide and the tool 21 forwardly or distally to position the prongs 39, or at least portions of the prongs, distally of the distal end 46 of the flexible member 45. Ultimately, the position control element 69 contacts the distal end of the slot 71 in the scope slide 53, and thereafter, forward sliding movement of the position control element drives both of the slides 49 and 53 distally to the extended position. During this phase of movement, both of the flexible members 19 and 45 are moved distally, and when the position control element engages the distal end of the slot 67 (FIG. 4), the distal end 46 and the tool 21 are out of the lumen 23, and the distal end 46 is more proximal than the tool as shown in FIG. 5.

The position control element 69 would ordinarily be advanced to the extended position after the catheter body 17 had been properly positioned adjacent the valves to be removed. The movement to the extended position advances the prongs 39 through the valves to cut and disrupt them. The distal end 46 is located proximally of the prongs 39 so as to not interfere with the cutting and disrupting action and to allow the physician a view of the surgical field.

Next, the position control element 69 can be retracted to the intermediate position of FIGS. 6 and 7. In this position, the position control element 69 is moved proximally until it contacts the proximal end of the slot 71. This motion of the position control element 69 withdraws the tubular flexible member 19 and the tool 21 while the flexible member 45 remains stationary. In the intermediate position of FIGS. 6 and 7, the tool 21 and the distal end 46 of the flexible member 45 are out of the catheter body 17 and, therefore, out of the lumen 23, and the distal end 46 is positioned distally of the tool 21. This gives the surgeon a better view of the surgical field following a first attempt at valve disruption. If desired, the position control element can be advanced to the extended position of FIGS. 4 and 5 repeatedly until the desired valve cutting action has been obtained. The position control element 69 is then returned to the retracted position of FIGS. 2 and 3 whereby the catheter body 17 can be advanced to the next vein to be disrupted or withdrawn from the vein.

The movement of the position control element 69 to all of the positions can be accomplished easily with one hand by simply manipulating the single position control element 69 with the thumb. With this embodiment, a single position control element 69 and the associated slides 49 and 53 bring about a preprogrammed movement of the tool 21 and the distal end 46. Also, with this embodiment, the endoscope 13 can be reused by detaching it from the control handle 15 using the adapter 57 as described above.

FIG. 9 shows an instrument 11a which is identical to the instrument 11 in all respects not shown or described herein. Portions of the instrument 11a corresponding to portions of the instrument 11 are designated by corresponding reference numerals followed by the letter "a." Functionally, the only difference between the two embodiments is that the endoscope for the instrument 11a cannot be removed from the control handle 15a. To accomplish this, the coupling 57a includes a flexible connector 81 having a passage 83 extending axially through it and partially received in a cavity of the scope slide 53a. The tube 43a is adhered within the passage 83 to the connector 81, and the flexible member 45a extends through the scope slide 53a in the same manner as shown above for the instrument 11. The operation of the instrument 11a is the same as that described above for the instrument 11.

FIGS. 10–13 show an instrument 11b which is identical to the instrument 11 in all respects not shown or described herein. Portions of the instrument 11b illustrated in FIGS. 10–13 corresponding to portions of the instrument 11 are designated by corresponding reference numerals followed by the letter "b."

Figure 11:
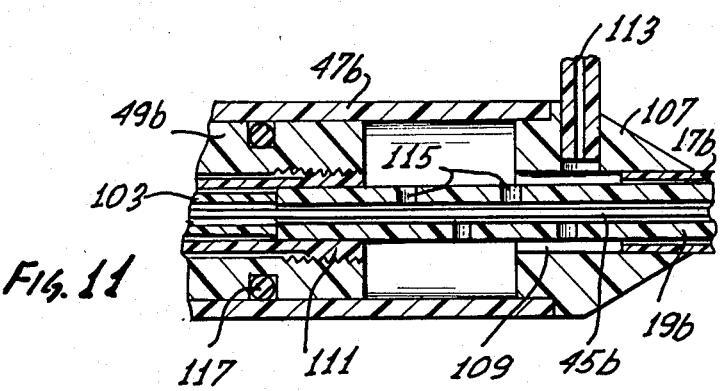
FIG. 11 is an enlarged fragmentary sectional view illustrating a distal region of the control handle of FIG. 10 with the position control element which controls the flexible member 45b moved distally from the position of FIG. 10.
Figure 12:
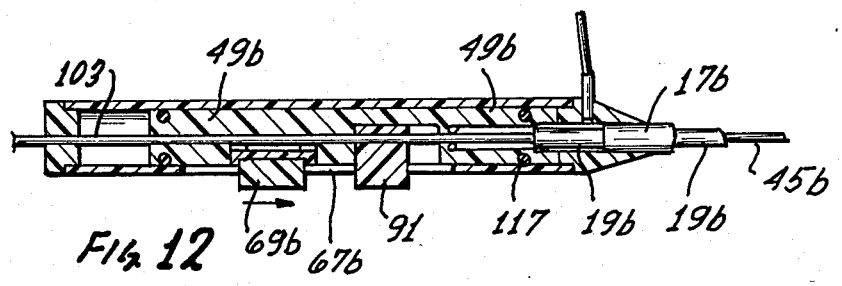
FIGS. 12 and 13 are sectional views similar to FIG. 10, with the position control elements in different positions.
Figure 13:
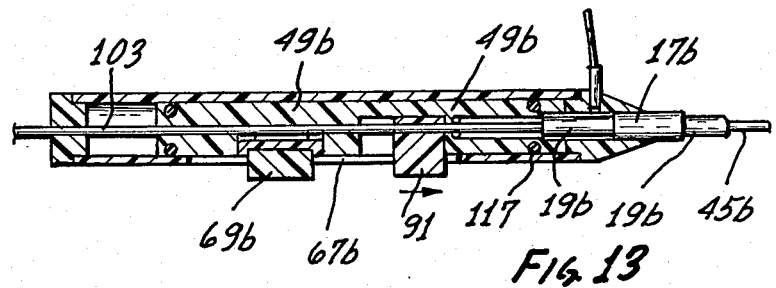

The primary difference between the instruments 11 and 11b is that the position controller of the instrument 11b includes two position control elements, i.e., the position control element 69b and 91. In addition, the position control element 91 serves also as the scope slide. Functionally, the use of two position control elements 69b and 91 increases the number of relative axial positions that can be assumed by the tool and the flexible member 45b (FIG. 11). On the other hand, the provision of the two position control elements 69b and 91 takes away the preprogrammed feature of the single position control element 69 of the instrument 11.

The sleeve 47b has its proximal end partially closed by an end cap 101. A rigid metal tube 103 is suitably coupled to the flexible tube 43b and is slidable in passages in the end cap 101 and in the tool slide 49b. The tube 103 is affixed to the position control element 91 in any suitable manner, such as an adhesive, and the flexible member 45b extends through the tubes 43b and 103 and is movable axially with these tubes by virtue of the small clearance between the flexible member 45b and the elongated flexible tube 43b.

The position control element 69 is suitably attached to the tool slide 49b, and it projects outwardly through the slot 67b. The tool slide 49 has a cavity 105 in which the position control element 91 is movable. The position control element 91 also projects outwardly through the slot 67b.

With reference to FIG. 11, the distal end of the sleeve 47b is partially closed by a plug 107 having an axial passage 109, and the catheter body 17b is partially received within the passage 109 and adhesively or otherwise attached to the plug. The tubular flexible member 19b is adhesively secured at its proximal end to a threaded attachment tube 111 which is threadedly coupled to the tool slide 49b. In FIG. 11, the position control element 91 is advanced distally to place the tube 103 in contact with the flexible member 19b. The position control element 69b can drive the flexible member 19b via the tool slide 49b and the tube 111. Similarly, the position control element 91 can drive the flexible member 45b. As shown in FIG. 11, the flexible member 45b extends coaxially through the flexible member 19b.

A saline flush can be supplied from a tube 113 and through radial ports 115 of the tubular flexible member 19b and out through the distal end of the member 19b. Annular seals 117 and 119 prevent the saline flush from moving proximally through the sleeve 47b.

Of course, the flexible member 45b terminates in a distal end 46 as shown in FIG. 3 for the instrument 11 and a tool, such as the tool 21 (FIG. 3) of the instrument 11 is coupled to the tubular flexible member 19b. Accordingly, the construction shown in FIG. 3 is also applicable to the instrument 11b.

FIG. 10 shows the position control elements 69b and 91 in their most proximal or retracted positions. Although the instrument 11b can be constructed to have this retracted position correspond to various different positions of the tool 21 and the distal end 46 (FIG. 3), in this embodiment, with the position control elements in the position of FIG. 10, the tool 21 and the distal end 46 are essentially in the position of FIG. 3, except that the distal end 46 is retracted proximally from the position shown in FIG. 3 such that it lies just proximal of the prongs 39.

To perform a vein disrupting operation of the type discussed above in connection with the instrument 11, the physician moves the position control element 69b distally to drive the flexible member 19b, the position control element 91 and the flexible member 45 distally to an extended position in which the distal end 46 and the prongs 39b are out of the catheter body essentially as shown in FIG. 5. If the physician wishes to advance the distal end 46 proximally of the prongs 39, he may do so by moving the position control element 91 distally to the position shown in FIG. 13. Alternatively, the physician may retract the position control element 69b while leaving the position control element 91 in the position of FIG. 12. Accordingly, the instrument 11b provides for greater flexibility in positioning of the tool 21 and the distal end 46 but does not have the full preprogramming features of the instrument 11.

Although exemplary embodiments of the invention have been shown and described, many changes, modifications and substitutions may be made by one having ordinary skill in the art without necessarily departing from the spirit and scope of this invention.

I claim:

1. An instrument comprising:
   an elongated control handle having a passage extending therethrough;
   an elongated, flexible catheter body having at least one lumen and a distal end;
   means for coupling the catheter body to the control handle;
   an elongated flexible member extending into said lumen and having a distal end portion;
   a tool coupled to the distal end portion of the flexible member, said tool being sized to be received in said lumen and being capable of performing a medical task within a patient;
   an elongated flexible image transmitting member extending through the passage and into the lumen;
   a position controller mounted for sliding movement along the control handle; and
   means for drivingly coupling the position controller to the flexible members so that the axial positions of the tool and the image transmitting member can be adjusted with respect to the distal end of the catheter body.

2. An instrument as defined in claim 1 wherein said means for coupling the position controller to the flexible members includes a slide mounted for sliding movement in the passage of the control handle and coupled to at least one of the flexible members and means for coupling the position controller to said slide.

3. An instrument as defined, in claim 1 wherein said control handle has a generally axially extending slot and said position controller projects through said slot.

4. An instrument as defined in claim 1 wherein the elongated flexible member having the tool coupled to it has a passage extending through it and the image transmitting member extends into the passage of such flexible member.

5. An instrument as defined in claim 1 wherein said coupling means includes first and second slides coupled to the flexible members, respectively, and mounted for sliding movement in said passage of the control handle, means for coupling the first slide to the position controller and means for coupling the second slide to the position controller with lost motion.

6. An instrument as defined in claim 5 wherein one of the slides is slidable within the other of the slides.

7. An instrument as defined in claim 5 including a flexible tube having the image transmitting member extending therethrough and means for releasably attaching the tube to the second slide with the tube extending proximally of the control handle.

8. An instrument as defined in claim 1 wherein the position controller includes first and second independently movable position control elements and said control means drivingly couples the first and second control elements to the flexible members, respectively.

9. An instrument as defined in claim 1 wherein the image transmitting member has a distal end, the position controller is movable from a retracted position to an extended position and then to an intermediate position between the extended and retracted positions and the coupling means for the flexible members positions the tool and the image transmitting member within the lumen in said retracted position, positions the tool and the distal end of the image transmitting member out of the lumen with the distal end of the image transmitting member more proximal than the tool in the extended position, and positions the tool and the distal end of the image transmitting member out of the lumen with the distal end of the image transmitting member positioned distally of the tool in the intermediate position.

10. An instrument comprising:
    a control handle;
    an elongated, flexible catheter body having at least one lumen and a distal end;
    means for coupling the catheter body to the control handle;
    an elongated flexible member extending into said lumen and having a distal end portion;
    a tool coupled to the distal end portion of the flexible member, said tool being sized to be received in said lumen and being capable of performing a medical task within a patient;
    an elongated flexible image transmitting member extending into the lumen and having a distal end;

a position control element mounted for movement on the control handle from a first position to a second position and then to an intermediate position between the first and second positions; and means for drivingly coupling the position control element to the flexible members such that the tool and the image transmitting member are within the lumen in the first position, the tool and the distal end of the image transmitting member are out of the lumen with the distal end of the image transmitting member being more proximal than the tool in the second position, and the tool and the distal end of the image transmitting member are out of the lumen with the distal end of the image transmitting member being positioned distally of the tool in the intermediate position.

11. An instrument as defined in claim 10 wherein the distal end of the image transmitting member is more distal than the tool in said first position.

12. An instrument as defined in claim 10 wherein the elongated flexible member having the tool coupled to it has a passage extending through it and the image transmitting member extends into the passage of such flexible member.

* * * * *